(12) United States Patent
Ji

(10) Patent No.: US 11,793,906 B2
(45) Date of Patent: Oct. 24, 2023

(54) BASE FILM FOR DRESSING AND MANUFACTURING METHOD THEREFOR, AND DRESSING COMPRISING THE BASE FILM

(71) Applicant: BOE TECHNOLOGY GROUP CO., LTD., Beijing (CN)

(72) Inventor: Chunyan Ji, Beijing (CN)

(73) Assignee: BOE TECHNOLOGY GROUP CO., LTD., Beijing (CN)

(*) Notice: Subject to any disclaimer, the term of this patent is extended or adjusted under 35 U.S.C. 154(b) by 640 days.

(21) Appl. No.: 16/756,256

(22) PCT Filed: Nov. 23, 2018

(86) PCT No.: PCT/CN2018/117245
§ 371 (c)(1),
(2) Date: Apr. 15, 2020

(87) PCT Pub. No.: WO2019/205613
PCT Pub. Date: Oct. 31, 2019

(65) Prior Publication Data
US 2021/0187154 A1    Jun. 24, 2021

(30) Foreign Application Priority Data
Apr. 26, 2018   (CN) .......................... 201810386416.X

(51) Int. Cl.
| | | |
|---|---|---|
| A61L 15/28 | (2006.01) | |
| A61F 13/00 | (2006.01) | |
| A61F 13/02 | (2006.01) | |
| A61L 15/44 | (2006.01) | |
| B32B 5/02 | (2006.01) | |
| B32B 5/26 | (2006.01) | |
| B32B 37/18 | (2006.01) | |

(52) U.S. Cl.
CPC ........ *A61L 15/28* (2013.01); *A61F 13/00029* (2013.01); *A61F 13/00063* (2013.01); *A61F 13/0286* (2013.01); *A61L 15/44* (2013.01); *B32B 5/024* (2013.01); *B32B 5/26* (2013.01); *B32B 37/18* (2013.01); *A61L 2300/104* (2013.01); *A61L 2300/404* (2013.01); *A61L 2400/12* (2013.01); *B32B 2535/00* (2013.01)

(58) Field of Classification Search
None
See application file for complete search history.

(56) References Cited

U.S. PATENT DOCUMENTS

| | | | |
|---|---|---|---|
| 2007/0056256 A1 | 3/2007 | Tepper et al. | |
| 2008/0167594 A1* | 7/2008 | Siniaguine | A61F 13/00995 |
| | | | 602/58 |
| 2008/0275409 A1 | 11/2008 | Kane et al. | |
| 2013/0018336 A1* | 1/2013 | Pernot | A61L 15/58 |
| | | | 424/445 |
| 2016/0000611 A1 | 1/2016 | Niederauer et al. | |
| 2019/0142642 A1 | 5/2019 | Burnet et al. | |

FOREIGN PATENT DOCUMENTS

| | | |
|---|---|---|
| CN | 101801311 A | 8/2010 |
| CN | 102631699 A | 8/2012 |
| CN | 102711850 A | 10/2012 |
| CN | 102908651 A | 2/2013 |
| CN | 103088630 A | 5/2013 |
| CN | 104588645 A | 5/2015 |
| CN | 105073077 A | 11/2015 |
| CN | 105497969 A | 4/2016 |
| CN | 205322859 U | 6/2016 |
| CN | 108578752 A | 9/2018 |
| KR | 10-2011-0076205 A | 7/2011 |
| TW | 201800069 A | 1/2018 |

OTHER PUBLICATIONS

International Search Report of PCT/CN2018/117245 in Chinese, dated Feb. 13, 2019, with English translation.
Chinese Office Action in Chinese Application No. 201810386416.X, dated Mar. 5, 2020 with English translation.

* cited by examiner

*Primary Examiner* — Robert A Wax
*Assistant Examiner* — Quanglong N Truong
(74) *Attorney, Agent, or Firm* — Collard & Roe, P.C.

(57) ABSTRACT

A base film for dressing and a manufacturing method thereof, and a dressing including the base film are provided. The base film includes a first region, including a composite fiber network of a micron fiber network and a nano fiber network; and a second region, including a micron fiber network. The composite fiber network in the first region and the micron fiber network in the second region are made of polymer materials.

19 Claims, 4 Drawing Sheets

BASE FILM FOR DRESSING AND MANUFACTURING METHOD THEREFOR, AND DRESSING COMPRISING THE BASE FILM

CROSS REFERENCE TO RELATED APPLICATIONS

This application is the National Stage of PCT/CN2018/117245 filed on Nov. 23, 2018, which claims priority under 35 U.S.C. § 119 of Chinese Application No. 201810386416.X filed on Apr. 26, 2018, the disclosure of which is incorporated by reference.

TECHNICAL FIELD

The present disclosure relates to a base film for dressing and a manufacturing method thereof, and a dressing including the base film.

BACKGROUND

Medical dressings currently used can be mainly divided into fabric dressings and plastic (resin-based) dressings. The fabric dressing, such as a band-aid made of a fabric material, is not waterproof, and is not tightly sealed relative to coated parts of a human body, which can easily cause wound infection. And the plastic dressing, such as a plastic film, is impermeable to moisture and air, which can easily lead to wound festering and deterioration over a long period of time.

Usually, an adhesive layer needs to be arranged in the dressing so as to be firmly attached to the skin. However, in a body fluid environment, such as infiltration of body fluids, and in an environment with relatively high humidity, and the like, the adhesive force of the adhesive layer will be destroyed, which causes the dressing to fall off, and the adhesive layer will bring discomfort to the user because of adhesion and tearing of the adhesive layer relative to the skin.

At present, although some antibacterial drugs are tried to be introduced into medical dressings, the material of the dressings has poor absorbability to antibacterial drugs, and the antibacterial drugs are easy to fall off and diffuse into the environment, which will affect healthy if ingested by the human body. This way not only wastes drugs, but also may lead to mass bacterial infection and worsen wounds.

Furthermore, medical dressings currently used usually cover or wrap the wound, medical personnel or other users cannot determine the positioning of the dressing relative to the wound upon applying the dressing, thus misalignment may occur, resulting in a situation that the coated wound area is not fully coated while the dressing is applied to normal peripheral tissues without coating, resulting in lower efficiency of the dressing. In addition, because the wound is wrapped, it is not convenient to check the wound healing. In order to check and confirm the wound condition, medical personnel or other users need to repeatedly remove the dressing and reapply it, which is easy to pull the wound and affect its recovery.

SUMMARY

At least one embodiment of the present disclosure provides a base film for dressing, which includes: a first region including a composite fiber network of a micron fiber network and a nano fiber network; and a second region including a micron fiber network, where the composite fiber network and the micron fiber network are made of polymer materials.

In some examples, the base film is transparent or translucent.

In some examples, the composite fiber network includes at least one of the following structures: the micron fiber network distributed with nano fiber dispersion; a network formed by intersecting micron fibers and nano fibers; and a lamination of the micron fiber network and the nano fiber network.

In some examples, the first region and the second region are made of any one or more of the group consisting of cellulose, cellulose derivatives, chitin and chitin derivatives.

In some examples, the first region is located in the middle of the base film, and surrounded by the second region.

In some examples, the composite fiber network of the first region further includes an antibacterial substance.

In some examples, the micron fiber network of the first region includes a blending fabric fiber of the antibacterial substance and micron fibers; or the antibacterial substance is added into the composite fiber network.

In some examples, the antibacterial substance includes silver nanoclusters.

In some examples, at least one of the composite fiber network in the first region and the micron fiber network in the second region is filled with cellulose gel particles.

In some examples, a microfluidic channel is provided in the second region.

In some examples, the second region includes a hydrophobic region, and the microfluidic channel is defined by the hydrophobic region.

In some examples, the second region includes a reagent region including a regent for detecting body fluid, and the reagent region is communicated with the microfluidic channel.

In some examples, the reagent includes the reagent for detecting any one or more of the group consisting of glucose, protein, nitrite, enzyme and tumor markers.

At least one embodiment of the present disclosure provides a dressing, which includes the base film as mentioned above.

In some examples, at least one of two opposite surfaces of the dressing is provided with a protective film.

At least one embodiment of the present disclosure provides a manufacturing method of a base film for dressing, which includes: forming a micron fiber network layer; and forming a composite fiber network layer of a micron fiber network and a nano fiber network in a part of the micron fiber network layer, so as to form a first region including the composite fiber network layer and a second region outside the composite fiber network layer.

In some examples, forming the composite fiber network layer includes at least one of the following steps: intersecting micron fibers and nano fibers; laminating the micron fiber network and the nano fiber network; and distributing nano fiber dispersion into the micron fiber network.

In some examples, distributing the nano fiber dispersion into the micron fiber network includes: applying a slurry containing the nano fiber dispersion to the micron fiber network, and pressing and drying the micron fiber network.

In some examples, the method further includes: preparing a silver nanocluster solution; applying the silver nanocluster solution to the composite fiber network layer; and washing and drying the composite fiber network layer.

In some examples, the silver nanocluster solution is prepared by any one of the group consisting of Brust- Schiffrin synthesis method, template method and precursor/ligand induced etching method.

In some examples, the silver nanocluster solution is obtained by mixing silver nitrate and an aqueous solution of a polymer, the polymer includes any one or more of the group consisting of polymethylacrylic acid, polymethylmethacrylate, polyvinylpyrrolidone and deoxyribonucleic acid.

In some examples, the method further includes: forming a hydrophobic photoresist layer in the micron fiber network layer of the second region; and patterning the photoresist layer to remove a part of the photoresist layer, to form a hydrophilic microfluidic channel in a region where the part of the photoresist layer is removed.

In some examples, the method further includes: adding a reagent in the second region to from a reagent region, where the reagent region is communicated with the microfluidic channel.

BRIEF DESCRIPTION OF THE DRAWINGS

In order to clearly illustrate the technical solution of embodiments of the present disclosure, the drawings of the embodiments will be briefly described in the following. It is obvious that the drawings in the description are only related to some embodiments of the present disclosure and not limited to the present disclosure.

FIG. 4 (b) illustrates a view of a microfluidic channel according to an embodiment of the present disclosure;

DETAILED DESCRIPTION

In order to make objects, technical details and advantages of the embodiments of the present disclosure apparent, the technical solutions of the embodiment will be described in a clearly and fully understandable way in connection with the drawings related to the embodiments of the present disclosure. It is obvious that the described embodiments are just a part but not all of the embodiments of the present disclosure. Based on the described embodiments herein, those skilled in the art can obtain other embodiment(s), without any inventive work, which should be within the scope of the present disclosure.

The terms "first," "second," etc., which are used in the present disclosure, are not intended to indicate any sequence, amount or importance, but distinguish various components. The terms "comprise," "comprising," "include," "including," etc., are intended to specify that the elements or the objects stated before these terms encompass the elements or the objects and equivalents thereof listed after these terms, but do not preclude the other elements or objects. The terms "upper," "lower," "left," "right," are only used to indicate the relative positional relationship, when the absolute position of the described object changes, the relative positional relationship may also change accordingly.

In the present disclosure, when a specific device is described to be located between the first device and the second device, an intervening device may or may not exist between the specific device and the first device, or between the specific device the second device. When it is described that the specific device is connected to other devices, the specific device may be directly connected to the other devices without the intervening device, or may be connected to the other devices through the inventing device instead of being directly connected to the other devices. As used in the present disclosure, the term "dressing" refers to various sheets applied to physiological sites, including but not limited to band-aids, adhesive films, stickers, etc.

All terms (including technical terms or scientific terms) used in the present disclosure have the same meaning as those understood by those skilled in the art to which the present disclosure belongs unless otherwise specifically defined. It should also be understood that terms defined in, for example, a general dictionary should be interpreted as having a meaning consistent with their meaning in the context of the related art, and should not be interpreted in an idealized or extremely formal sense unless explicitly defined herein.

Technologies, methods and devices known to those skilled in the relevant art may not be discussed in detail, but where appropriate, the technologies, methods and devices should be considered as part of the specification.

Figure 1:
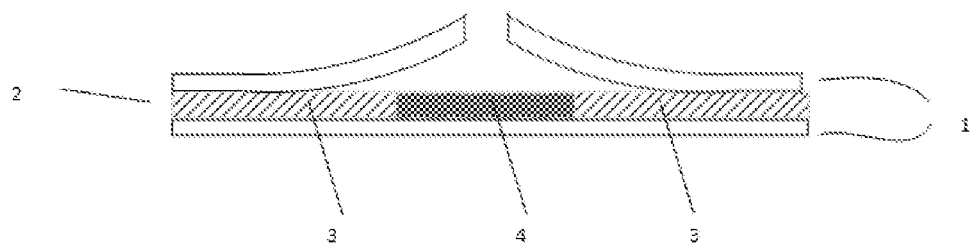
FIG. 1 illustrates a sectional view of a dressing according to an embodiment of the present disclosure.

FIG. 1 illustrates a sectional view of a dressing according to an embodiment of the present disclosure. The dressing includes a base film 2, the base film 2 is made of polymer materials, and is a network structure by intersecting fibers. In some embodiments, the dressing further includes an encapsulation portion except the base film 2, so as to facilitate encapsulation and transportation of the base film 2. For example, as illustrated in FIG. 1, the dressing can include the base film 2 and two isolation protective films 1 located on upper and lower sides of the base film 2. The encapsulation portion can adopt other arrangement, such as packaging bags, etc. For example, the encapsulation portion herein can refer to a protective film, which can be disposed on at least one surface of the base film 2.

Figure 2:
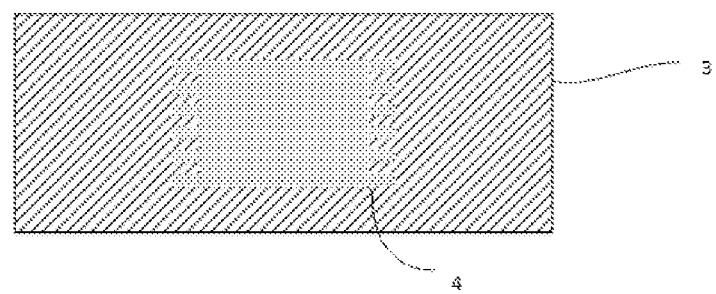
FIG. 2 illustrates a top view of the dressing shown in FIG. 1.

As illustrated in FIG. 1 and FIG. 2, the base film 2 includes: a first region 4, which includes a composite fiber network of a micron fiber network and a nano fiber network; and a second region 3, which includes a micron fiber network. The first region 4 including the composite fiber network of the micron fiber network and the nano fiber network in the base film 2 of the dressing has the following advantages: large specific surface area and good surface absorbability, which are beneficial to the adsorption and slow release of antibacterial substances on its surface; high surface porosity and good air permeability which is favorable for wound recovery.

For example, the micron fiber network refers to that a pore size of a pore in the network is of the micrometer scale, and the nano fiber network refers to a pore size of a pore in the network is of the nanometer scale.

Although the abovementioned embodiments take an example that the first region is the composite fiber network of the micron fiber network and the nano fiber network, and the second region is the micron fiber network for description, but the embodiments of the present disclosure include but are not limited thereto, the second region can also include a nano fiber network.

The base film 2 is composed of the fiber network, and the film composed of the fiber network can form a good covering contact with the skin only by slightly wetting, thus, the dressing does not need an adhesive layer. Even though the base film 2 is continuously soaked in the body fluid environment, the base film 2 can be kept in a wet state, so as to be able to maintain a good covering contact with the skin without falling off. By getting rid of the dependence on the adhesive layer, the base film 2 of the dressing increases the use comfort of the user, the user does not have to endure the pain of tearing the skin by the adhesive layer upon removing the dressing, and the base film 2 of the dressing can repeatedly cover the wound. As long as the base film 2 of the dressing is kept wet, the good covering contact can still be maintained, and the covering contact cannot be influenced due to the failure of the adhesive layer. In some embodiments, the base film 2 can be coted with a wet agent, such as glycerin, to increase the hydrophilicity of the surface of the base film 2, thereby effectively prolonging the application time.

In some embodiments, the base film 2 can be made to have a smaller thickness, for example, a thickness of about 100-200 microns, thereby further increasing air permeability and coating comfort. The light and thin base film 2 in cooperation with the covering contact effect of the wetting fiber base on the skin can enable the dressing to be more tightly and firmly attached to a part to be coated, such as the skin.

In some embodiments, the base film 2 can be transparent or translucent.

In some embodiments, the first region 4 and the second region 3 can use any one or more of the group consisting of cellulose, cellulose derivatives, chitin and chitin derivatives as raw materials. The raw materials are easily obtained, for example, the raw materials can be extracted from natural materials, which have low cost and excellent biocompatibility and degradation performance. The base film 2 is usually made to be transparent or translucent, which is convenient for users to observe the wound recovery status in real time through the dressing. In some embodiments, the materials of the first region 4 and the second region 3 are both selected to be cellulose fibers, a large number of hydroxyl groups on a surface of the cellulose fibers have natural hydrophilicity and are convenient to adhere to wounds overflowing body fluids. The composite fiber network in the abovementioned first region 4 can be formed in various manners, for example, the composite fiber network can be formed by intersecting micron fibers and nano fibers, can be formed by laminating the micron fiber network and the nano fiber network, or can also be formed by adding nano fiber dispersion into the micron fiber network.

In some embodiments, the nano fiber network is formed by nano fiber dispersion distributed in the micron fiber network. For example, the micron fiber network can be first formed as a base material of the first region 4, and then the nano fiber dispersion can be filled into the micron fiber network of the first region 4 by any one or more manners of soaking, casting, spraying, coating and the like to form the nano fiber network. In this way, by filling micron pores with nano fiber dispersion, the number of the micron pores is reduced, so as to reduce the pore size, thereby reducing light scattering (if the pore size is small enough, even light scattering can be avoided), improving transmittance, and further improving local transparency. The first region 4 having sufficient transparency can be used as an observation window to facilitate the user to accurately locate the wound upon applying the dressing, and also to facilitate the user to observe the healing or inflammation of the wound at any time after applying the dressing without repeatedly uncovering the dressing, thereby contributing to the recovery of the wound. In some embodiments, the nano fiber dispersion is filled in a liquid environment, for example, the material of the first region 4 is immersed in the slurry (such as suspension) of the nano fiber dispersion, while the periphery of the first region 4 can be compressed upon filling (pouring) the nano fiber dispersion, to prevent the slurry and the nano fiber dispersion included in the slurry from infiltrating into other regions, such as the second region 3, and the compaction is released after being pressed to dry and form.

As illustrated in FIG. 2, as an example, the first region 4 is located in a center region of the base film 2, that is, the second region 3 can surround the first region 4. Because the dressing is usually applied around the wound, that is, the wound is usually located in the center of the dressing, the first region is disposed near the center of the dressing, so that upon the first region 4 being used as an observation window, the condition of the wound can be observed more completely and clearly. But relative positions of the first region 4 and the second region 3 are not limited thereto, and can be adjusted according to specific requirement. It should be noted that, the "center" position here is not the right middle position, and the first region 4 can be located at any suitable position in the middle of the base film 2. Furthermore, the second region 3 surrounds the first region 4, which does not mean that the second region 3 must completely surround the first region 4, and can also mean that the second region 3 can be partially disposed at the periphery of the first region 4.

In some embodiments, the composite fiber network of the first region 4 further includes antibacterial substances, the antibacterial substances and the micron fiber are blended and woven into fibers for forming the micron fiber network of the first region (which may be referred to as a filling-type processing method), that is, the micron fiber network of the first region 4 includes a blending fabric fiber of the antibacterial substances and the micron fibers; or after forming the composite fiber network, the antibacterial substances are added to the composite fiber network (which may be referred to as a post-processing method), that is, the antibacterial substances are added to the composite fiber network. The dressing obtained by the filling-type processing method (especially the first region 4) has higher adhesion of antibacterial substances and longer antibacterial effect, is especially suitable for using repeatedly, has higher cleaning resistance, and is not easy to lose antibacterial property because of cleaning treatment such as washing and disinfection. The post-processing method combines antibacterial substances on the fiber surface through chemical bonds and hydrogen bonds after the fiber network is formed, and is generally suitable for disposable dressings, and has poor cleaning resistance, but is relatively simple to process and low in cost.

The antibacterial substances can include antibacterial drugs (such as nano particles), and can also include nano particles with antibacterial effect, including but not limited to nano silver materials, chitosan and derivatives thereof, etc. The nano silver material has excellent antibacterial property, and has the following characteristics: broad spectrum antibacterial, powerful sterilization, strong permeability, repair regeneration, durable antibacterial and no drug resistance. Chitosan and its derivatives have outstanding antibacterial activity, good biodegradability, biocompatibility, moisture absorption and moisture retention, and are environment-friendly antibacterial agents, which have antibacterial properties against yeast, mold, gram-positive and gram-negative bacteria. By using any one or more of nano silver materials, chitosan and derivatives thereof as the antibacterial substances in the composite fiber network, corresponding beneficial antibacterial effects can be realized.

In some embodiments, various antibacterial substances can be combined into the nano fiber network of the composite fiber network by corresponding methods. For example, for chitosan and its derivatives, chitosan fibers can be uniformly covered into the nano fiber network composed of bacterial cellulose by an electrostatic spinning method, or a polyelectrolyte composite nano fiber network with antibacterial properties can be obtained by taking an oxidized bacterial cellulose nano fiber network (with negative charges) as a base film and using electrostatic action between anionic polyelectrolytes and cationic polyelectrolytes to act on chitosan cationic polymers.

Figure 3:
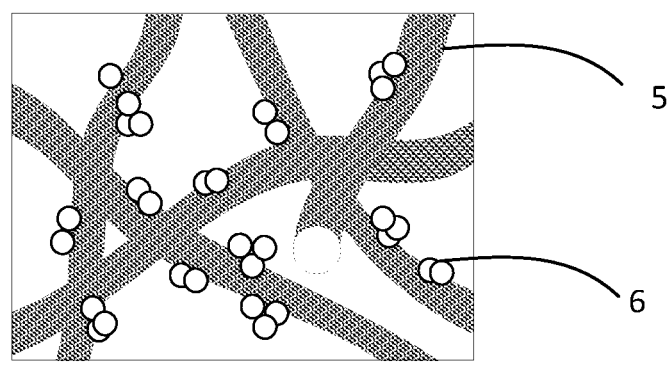
FIG. 3 illustrates a schematic view of an internal microstructure in a first region of a dressing according to an embodiment of the present disclosure.

In some embodiments, the nano silver material includes silver nanoclusters, the energy level splitting and quantum size effect caused by a small size of silver nanoclusters make them have obvious fluorescence effect, which not only has the sterilization effect of common nano silver materials, but also can emit fluorescence at 622 nm wavelength to indicate the sterilization condition. The silver nanoclusters can be adsorbed into the nano fiber network by preparing a silver nanocluster solution and soaking the film with the silver nanocluster solution, and washing and drying the soaked film. A local microscopic schematic diagram of the nano fiber network with the silver nanoclusters adsorbed is shown in FIG. 3, in which the silver nanoclusters 6 are dispersed and adsorbed on a fiber chain 5 of the nano fiber network in the first region 4. Because of a large specific surface area of the fiber base film, enough silver nanoclusters 6 can be adsorbed by hydrogen bonds. By doping the particles on the fiber chain 5, the first region 4 is colored (e.g., pink), and the user can judge a bacteria killing condition of the wound according to the depth change of the color of pink. The first region 4 including the silver nanoclusters 6 can effectively inhibit the growth of colonies, and the fluorescence intensity decreases with the decrease of bacterial concentration.

In some embodiments, at least one of the composite fiber network in the first region 4 and the micron fiber network in the second region 3 of the dressing is filled with cellulose gel particles to further improve blood absorption capability, further maintain dryness of the dressing and the wound, and effectively prevent a problem of adhesion between the dressing and the wound.

In some embodiments, the materials of the first region and the second region have moderate hydrophilicity, for example, the cellulose as the raw material can be modified with natural polysaccharide molecules to avoid excessive swelling of the dressing.

Figure 4A:
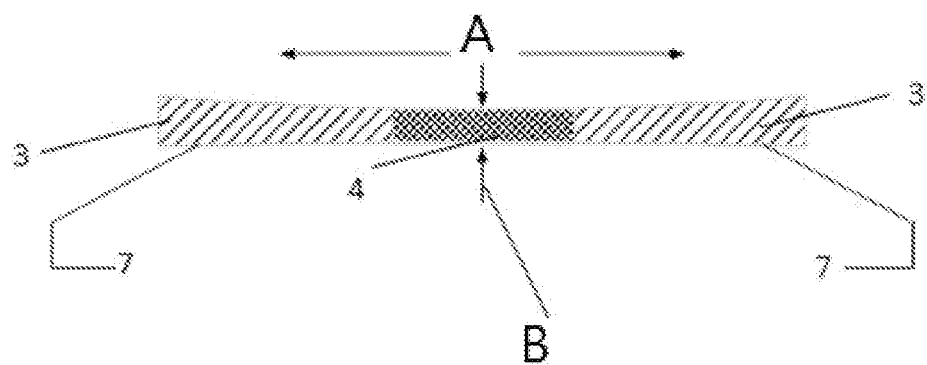
FIG. 4 (a) illustrates a view of a process of in-situ detection of overflow fluid of wound using a dressing according to an embodiment of the present disclosure.
Figure 4B:
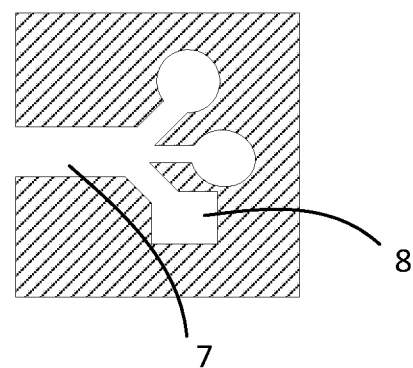

In some embodiments, overflow liquid of the wound can be collected in the second region 3 for in-situ detection and components of the overflow liquid can be analyzed. The second region 3 is formed of the micron fiber network, the micron fiber network forms micron pores as natural capillary channels, which can drive the overflow liquid through capillary action of the capillary channels without the need for an additional driving pump, thereby facilitating the collection and analysis of the overflow liquid. As illustrated in FIG. 4 (a), by pressing the first region 4 in a pressing direction B shown, the capillary action of the micron fiber network of the second region 3 drives the overflow liquid to flow to the second region 3 along the fluid driving direction A. In some embodiments, the reagent can be combined in the micron fiber network of the second region 3 in various ways similar to the combination of the antibacterial substances and the fiber network, so that the dressing acts as a test paper. The detection results of any one or various components, such as glucose, protein, nitrite, enzyme and tumor marker, are obtained by reacting various components in the overflow liquid flowing into the second region 3 with the reagents to generate various labeling effects, such as but not limited to color development, luminescence, etc.

In some embodiments, a microfluidic channel 7 can be formed in the second region 3, for example, the microfluidic channel 7 can be formed in a lower surface of the second region 4. As illustrated in FIG. 4 (b), the overflow liquid flowing to the second region 3 can flow according to the arrangement of the microfluidic channel 7 through the quantitative arrangement of the microfluidic channel 7, so as to facilitate the quantitative detection of various components of the overflow liquid. Furthermore, a flexible arrangement of the microfluidic channel 7 can be used to realize various conditions required for detection of overflow liquid. For example, assuming that multi-index detection of the overflow liquid is to be realized, multi-branch microfluidic channels 7 can be set. When different branches need different arrival times of the overflow liquid (e.g., different reaction times with reagents), liquid level differences can be set for different branches.

Thus, the dressing provided with the microfluidic channel 7 in the second region 3 can be used as a paper chip, and can be applied to the detection of various clinical analytes in blood and body fluids, such as glucose, protein, nitrite, enzyme, tumor markers, etc., in combination with detection technologies such as optical detection means (colorimetric method, fluorescence method, chemiluminescence method, surface enhanced Raman spectroscopy, etc.), electrochemical detection means, or combination of any one or more of these means, so as to provide a new analysis platform for early diagnosis and treatment, and clinical detection.

In some embodiments, a reaction regent region 8 can be disposed in the second region 3, the reaction regent region 8 includes a reagent for detecting any one or more of the group consisting of glucose, protein, nitrite, enzyme and tumor marker in the body fluid flowing through the microfluidic channel 7. The reaction regent can be in combination with the micron fiber network in the second region 3 in advance before the microfluidic channel 7 is formed in various ways similar to the combination of the antibacterial substances with the fiber network. The body fluid flowing into the microfluidic channel 7 reacts with the contacted reaction regent to develop color, which can be used for diagnosing diseases and has low cost. In some embodiments, different reaction regent regions 8 can be disposed into different second regions 3, or different reaction regent regions 8 can be disposed into different branches of the microfluidic channel 7 in the same second region 3, so as to obtain detection results of various clinical analytes such as any one or more of glucose, protein, nitrite, enzyme and tumor markers at one time.

Figure 5:
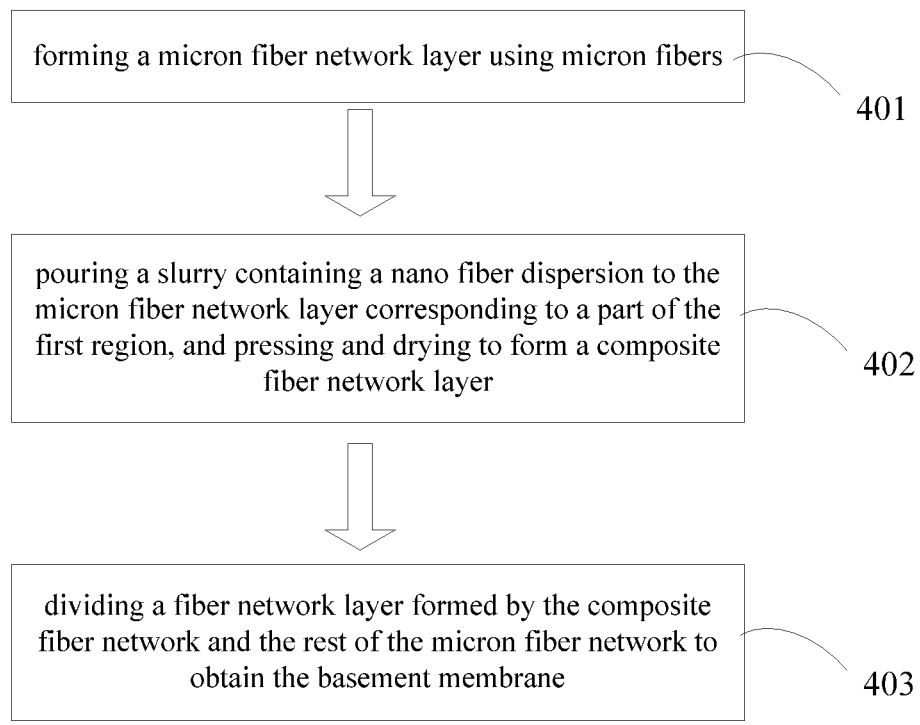
FIG. 5 illustrates a flow chart of a method for manufacturing a base film of a dressing according to an embodiment of the present disclosure.

FIG. 5 illustrates a flow chart of a method for manufacturing a base film of a dressing according to the fourth embodiment of the present disclosure. As illustrated in FIG. 5, the method includes: forming a micron fiber network layer using micron fibers (step 401), pouring a slurry containing a nano fiber dispersion to a part of the micron fiber network layer corresponding to the first region, and pressing and drying to form a composite fiber network layer (step 402); and dividing a fiber network layer formed by the composite fiber network and the rest of the micron fiber network to obtain the base film (step 403). The method can conveniently manufacture the base film in batch.

In some embodiments, before the division step, the manufacturing method of the base film 2 further includes the following steps: preparing a silver nanocluster solution; soaking a part of the composite fiber network layer corresponding to the first region in the silver nanocluster solution; and then washing and drying the part of the composite fiber network layer after soaking. Thus, the silver nanoclusters 6 can be fully dispersed and adsorbed into the nano fiber network in a simple manner, so that the manufactured base film not only has spectral sterilization effect, but also can present different fluorescent color development according to bacteria killing conditions, therefore, a user can intuitively judge the bacteria killing conditions of the wound according to the depth change of pink color. As an example, the following specific process can be adopted to fully disperse and adsorb the silver nanoclusters 6 into the nano fiber network: mixing silver nitrate and polymethacrylic acid at a preferred molar ratio of 4:1 to obtain the silver nanocluster solution with a diameter of less than 2 nm; soaking the fiber base film in an aqueous solution of the silver nanocluster wrapped by polymethacrylic acid for several hours, and then washing the base film with deionized water and pressing and drying the base film.

The silver nanocluster solution can be prepared by various methods. In some embodiments, the various methods include any one of the group consisting of Brust-Schiffrin synthesis method, template method and precursor/ligand induced etching method. As an example, the silver nanocluster solution can be obtained by mixing silver nitrate and an aqueous solution of a polymer, the polymer includes any one or more of the group consisting of polymethylacrylic acid, polymethylmethacrylate, polyvinylpyrrolidone and deoxyribonucleic acid.

In some embodiments, before the division step, the manufacturing method of the base film 2 further includes forming a microfluidic channel 7 on a lower surface of the second region 3 of the base film 2. In some embodiments, the microfluidic channel 7 can be formed by using a curable hydrophobic material including, but not limited to, wax, photoresist, long carbon chain alkyl silane (e.g., octadecyltrichlorosilane), alkyl ketene dimer, and the like, and corresponding processes include, but not limited to, photolithography, printing, hand drawing, and the like. For example, a hydrophobic region formed by the hydrophobic material defines the microfluidic channel.

Figure 6:
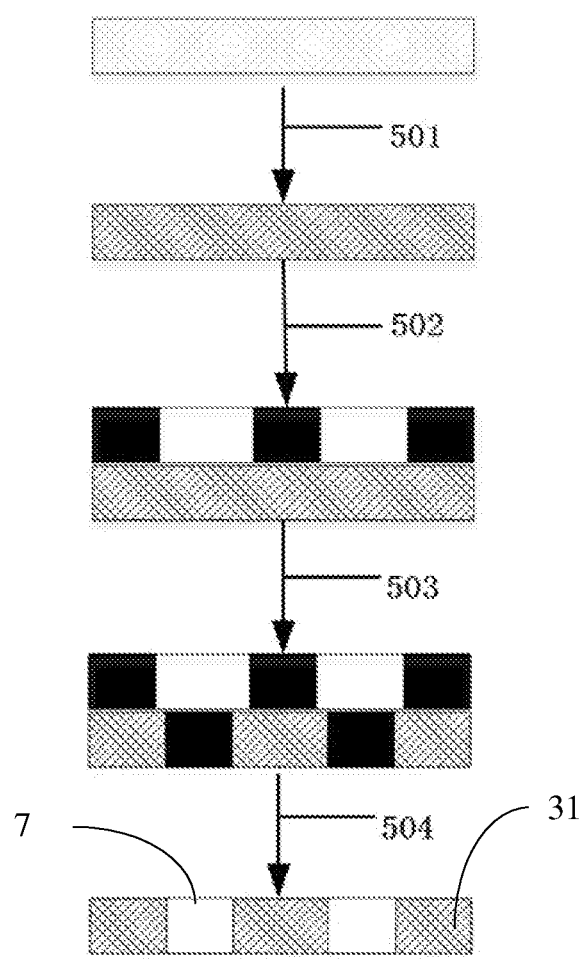
FIG. 6 illustrates a view of a process flow of forming a microfluidic channel on a lower surface of a second region in a base film of a dressing according to an embodiment of the present disclosure.

FIG. 6 illustrates a view of a process flow of forming the microfluidic channel 7 on the lower surface of the second region 3 in the base film 2 of the dressing according to the fifth embodiment of the present disclosure. As illustrated in FIG. 6, the process flow includes the following steps: applying a hydrophobic photoresist layer on a surface of the another part of the fiber network layer corresponding to the second region 3 of the base film 2 (step 501); laminating a mask on the photoresist layer (step 502); exposing the lamination of the another part and the photoresist layer via the mask, such as ultraviolet light degradation, etc. (step 503); removing the mask and developing the photoresist layer to form the microfluidic channel 7 (step 504). The photoresist layer may use any one of positive photoresist and negative photoresist. The positive photoresist is used as an example in the process flow in FIG. 6. As illustrated in FIG. 6, in step 503, an exposed part of the photoresist layer undergoes photochemical reaction; in step 504, the exposed part of the photoresist layer is dissolved in the developer, while an unexposed portion remains on the surface of the another part of the formed fiber network layer corresponding to the second region 3 of the base film 2, thereby forming the microfluidic channel 7. For example, the remaining part of the photoresist layer forms a hydrophobic region 31, as illustrated in FIG. 6. For example, the abovementioned step 503 and 504 are patterning processes of the photoresist layer. For example, the region where the photoresist is removed corresponds to the region where the microfluidic channel is formed.

In the present disclosure, a rectangular dressing shown in the figure is only an example, and other abnormal-shaped dressings as variations thereof should be included in the scope of protection of the present patent.

Furthermore, although exemplary embodiments have been described herein, the scope of the embodiments includes any and all embodiments based on the present disclosure having equivalent elements, modifications, omissions, combinations (e.g., technical solutions where various embodiments intersect), adaptations, or variations. Elements in the claims are to be interpreted broadly based on the language employed in the claims, and are not limited to the examples described in the specification or during the implementation of the application, and examples thereof are to be interpreted as non-exclusive. Therefore, the specification and examples are intended to be considered as examples only, a true scope and spirit are indicated by the following claims and the full scope of equivalents thereof.

The above description is intended to be illustrative and not limiting. For example, the above examples (one or more technical solutions) may be used in combination with each other. For example, other embodiments may be used by those skilled in the art upon reading the above description. In addition, in the above-described specific embodiments, various features may be grouped together to simplify the present disclosure. It should not be interpreted as an intention that an unclaimed disclosed feature is essential to any claim. On the contrary, the subject matter of the present invention may be less than all features of a particular disclosed embodiment. Thus, the following claims are hereby incorporated into the specific embodiments as examples or embodiments, where each claim is independently taken as a separate embodiment, and it is contemplated that these embodiments may be combined with each other in various combinations or permutations.

What are described above is related to the illustrative embodiments of the disclosure only and not limitative to the scope of the disclosure; the scopes of the disclosure are defined by the accompanying claims.

What is claimed is:
1. A base film for dressing, comprising:
a first region, comprising a composite fiber network of a micron fiber network and a nano fiber network; and
a second region, comprising a micron fiber network,
wherein the composite fiber network in the first region and the micron fiber network in the second region are made of polymer materials,
the first region and the second region are different regions arranged in a lateral direction of the base film, and the first region is located in the middle of the base film and surrounded by the second region, and
a pore size of a pore in the composite fiber network of the first region is different from that in the micron fiber network of the second region.
2. The base film according to claim 1, wherein the base film is transparent or translucent.

3. The base film according to claim 1, wherein the composite fiber network comprises at least one of the following structures:
   the micron fiber network distributed with nano fiber dispersion;
   a network formed by intersecting micron fibers and nano fibers; and
   a lamination of the micron fiber network and the nano fiber network.

4. The base film according to claim 1, wherein the first region and the second region are made of any one or more of the group consisting of cellulose, cellulose derivatives, chitin and chitin derivatives.

5. The base film according to claim 1, wherein the composite fiber network of the first region further comprises an antibacterial substance.

6. The base film according to claim 5, wherein the micron fiber network of the first region comprises a blending fabric fiber of the antibacterial substance and micron fibers; or the antibacterial substance is added into the composite fiber network.

7. The base film according to claim 5, wherein the antibacterial substance comprises silver nanoclusters.

8. The base film according to claim 1, wherein at least one of the composite fiber network in the first region and the micron fiber network in the second region is filled with cellulose gel particles.

9. The base film according to claim 1, wherein a microfluidic channel is provided in the second region.

10. The base film according to claim 9, wherein the second region comprises a hydrophobic region, and the microfluidic channel is defined by the hydrophobic region.

11. The base film according to claim 9, wherein the second region comprises a reagent region including a reagent for detecting body fluid, and the reagent region is communicated with the microfluidic channel.

12. The base film according to claim 11, wherein the reagent comprises a reagent for detecting any one or more of the group consisting of glucose, protein, nitrite, enzyme and tumor markers.

13. A dressing, comprising the base film according to claim 1.

14. The dressing according to claim 13, wherein at least one of two opposite surfaces of the dressing is provided with a protective film.

15. A manufacturing method of a base film for dressing, comprising:
   forming a micron fiber network layer; and
   forming a composite fiber network layer of a micron fiber network and a nano fiber network in a part of the micron fiber network layer, so as to form a first region including the composite fiber network layer and a second region outside the composite fiber network layer,
   wherein the first region and the second region are different regions arranged in a lateral direction of the base film, and the first region is located in the middle of the base film and surrounded by the second region, and
   a pore size of a pore in the composite fiber network of the first region is different from that in the micron fiber network of the second region.

16. The manufacturing method of the base film for dressing according to claim 15, wherein forming the composite fiber network layer comprises at least one of the following steps:
   intersecting micron fibers and nano fibers;
   laminating the micron fiber network and the nano fiber network; and
   distributing nano fiber dispersion into the micron fiber network.

17. The manufacturing method of the base film for dressing according to claim 16, wherein distributing the nano fiber dispersion into the micron fiber network comprises:
   applying a slurry containing the nano fiber dispersion to the micron fiber network, and pressing and drying the micron fiber network.

18. The manufacturing method of the base film for dressing according to claim 15, further comprising:
   preparing a silver nanocluster solution;
   applying the silver nanocluster solution to the composite fiber network layer; and
   washing and drying the composite fiber network layer.

19. The manufacturing method of the base film for dressing according to claim 15, further comprising:
   forming a hydrophobic photoresist layer in the micron fiber network layer of the second region; and
   patterning the photoresist layer to remove a part of the photoresist layer, to form a hydrophilic microfluidic channel in a region where the part of the photoresist layer is removed.

* * * * *